(12) United States Patent
Ansmann et al.

(10) Patent No.: US 7,875,740 B2
(45) Date of Patent: Jan. 25, 2011

(54) IRON-CONTAINING MATERIAL SUITABLE FOR USE AS HYDROGENATION CATALYST

(75) Inventors: Andreas Ansmann, Wiesloch (DE); Christoph Benisch, Mannheim (DE); Peter Baβler, Viernheim (DE); Rolf-Hartmuth Fischer, Heidelberg (DE); Stefan Maixner, Schwetzingen (DE); Johann-Peter Melder, Böhl-Iggelheim (DE); Hermann Luyken, Ludwigshafen (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 760 days.

(21) Appl. No.: 10/493,419

(22) PCT Filed: Oct. 18, 2002

(86) PCT No.: PCT/EP02/11669
§ 371 (c)(1), (2), (4) Date: Apr. 22, 2004

(87) PCT Pub. No.: WO03/035250
PCT Pub. Date: May 1, 2003

(65) Prior Publication Data
US 2004/0254059 A1    Dec. 16, 2004

(30) Foreign Application Priority Data
Oct. 23, 2001  (DE) .................. 101 51 559

(51) Int. Cl.
*C07C 255/03* (2006.01)
*C07C 209/04* (2006.01)
(52) U.S. Cl. ............... 558/459; 564/491; 564/492; 564/493
(58) Field of Classification Search ......... 564/491, 564/492, 493; 558/459
See application file for complete search history.

(56) References Cited

U.S. PATENT DOCUMENTS

| | | | |
|---|---|---|---|
| 3,338,704 A | 8/1967 | Laurent et al. | |
| 3,696,153 A | 10/1972 | Kershaw et al. | |
| 4,064,172 A | 12/1977 | Dewdney et al. | |
| 4,714,641 A | 12/1987 | Cordts | |
| 5,137,783 A | 8/1992 | Tanihara et al. | |
| 5,527,946 A | 6/1996 | Flick et al. | |
| 5,846,507 A | 12/1998 | Liu et al. | |
| 6,222,059 B1 | 4/2001 | Ebel et al. | |
| 6,297,394 B1 * | 10/2001 | Voit et al. ........... | 558/459 |

OTHER PUBLICATIONS

Weissermel/Arpe, Industrielle Organische Chemic, Verlag Chemie, 3. Auflange, 1988, Seite 266.

* cited by examiner

*Primary Examiner*—James O Wilson
*Assistant Examiner*—Ebenezer Sackey
(74) *Attorney, Agent, or Firm*—Novak Druce + Quigg LLP

(57) ABSTRACT

The iron-containing catalyst suitable for use as a catalyst contains a) iron or a mixture containing iron and an iron-based compound. The iron has an average crystallite size ranging from 1-35 nm measured by X-ray diffraction.

20 Claims, No Drawings

IRON-CONTAINING MATERIAL SUITABLE FOR USE AS HYDROGENATION CATALYST

The present invention relates to a composition which is suitable as a catalyst and comprises a) iron or a mixture comprising iron and a compound based on iron, wherein the iron has an average mean crystallite size in the range from 1 to 35 nm, measured by means of X-ray diffraction.

The invention further relates to a process for preparing such a composition and to a process for hydrogenating a nitrile group in a compound containing a nitrile group to form an amino group in the presence of such a composition as catalyst.

It is generally known, for example from Weissermel/Arpe, Industrielle Organische Chemie, Verlag Chemie, 3rd edition, 1988, page 266, or WO-A-96/20166, that adiponitrile can be hydrogenated in the presence of a catalyst comprising predominantly iron to give a mixture of 6-aminocapronitrile and hexamethylenediamine or hexamethylenediamine alone.

6-Aminocapronitrile and hexamethylenediamine are important intermediates for the preparation of industrially important polymers such as Nylon 6 or Nylon 6.6.

It is desirable for the catalyst to have a high mechanical strength and a long operating life and to give a high space-time yield of the desired products 6-aminocapronitrile and hexamethylenediamine or hexamethylenediamine alone. In particular, the catalyst should give a very low level of undesirable by-products in this hydrogenation.

Such undesirable by-products can be separated from the desired product only with difficulty.

Thus, for example, the hydrogenation of adiponitrile to 6-aminocapronitrile and hexamethylenediamine forms variable amounts of, inter alia, tetrahydroazepine (THA), 1-amino-2-cyanocyclopentene (ICCP), 2-aminomethylcyclopentylamine (AMCPA), 1,2-diaminocyclohexane (DCH) and bishexamethylenetriamine (BHMTA). It is known from U.S. Pat. No. 3,696,153 that AMCPA and DCH can be separated from hexamethylenediamine only with great difficulty. In addition, large amounts, in particular, of AMCPA, DCH and THA lead to the need for an elaborate distillation, which is reflected in considerable capital and energy costs.

WO 98/11059 discloses a process for preparing alpha, omega-aminonitriles by hydrogenation of the corresponding nitriles over iron-containing catalysts which process displays high catalyst operating lives and selectivities and also makes low by-product concentrations possible. Thus, in example 2, a total selectivity of 98.9% of hexamethylenediamine and 6-aminocapronitrile at a DCH content of 3700 ppm, an AMCPA content of 430 ppm and an ICCP content of 80 ppm based on HMD is achieved at 80° C. A disadvantage of the process disclosed is the low conversion of adiponitrile which at 80° C. is only 47.3%. Thus, the space-time yield of this process is unsatisfactory.

It is an object of the present invention to provide iron-containing compositions which are suitable as catalysts and in whose presence it is possible to hydrogenate nitriles to amines in a simple manner while avoiding the above-mentioned disadvantages.

We have found that this object is achieved by the compositions defined at the outset, a process for preparing them and a process for hydrogenating a nitrile group in a compound containing a nitrile group to form an amino group in the presence of such a composition as catalyst.

According to the present invention, the iron in the compositions has an average mean crystallite size of at least 1 nm, preferably at least 5 nm, in particular at least 10 nm.

According to the present invention, the iron in the compositions has an average mean crystallite size of not more than 35 nm, preferably not more than 30 nm.

For the purposes of the present invention, the average mean crystallite size is as determined by X-ray diffraction on a D5000 theta/theta diffractometer (from Siemens, Germany) using TOPAS software for evaluation.

In a further preferred embodiment, the oxidic composition can further comprise c) from 0 to 0.5% by weight, preferably from 0.05 to 0.4% by weight, in particular from 0.1 to 0.2% by weight, based on a), of a compound based on an alkali metal or alkaline earth metal preferably selected from the group consisting of lithium, sodium, potassium, rubidium, cesium, magnesium and calcium and mixtures thereof.

In a further preferred embodiment, the oxidic composition can further comprise b) from 0.01 to 5% by weight, preferably from 0.5 to 4% by weight, in particular from 1 to 3% by weight, based on a), of a promoter based on 1, 2, 3, 4 or 5 elements selected from the group consisting of aluminum, silicon, zirconium, titanium and vanadium, in particular a promoter based on 1, 2 or 3 elements selected from the group consisting of aluminum, silicon and titanium, and c) from 0 to 0.5% by weight, preferably from 0.05 to 0.4% by weight, in particular from 0.1 to 0.2% by weight, based on a), of a compound based on an alkali metal or alkaline earth metal preferably selected from the group consisting of lithium, sodium, potassium, rubidium, cesium, magnesium and calcium.

In a further preferred embodiment, the oxidic composition can further comprise d) from 0.001 to 1% by weight, preferably from 0.001 to 3% by weight, in particular from 0.01 to 0.2% by weight, based on a), of manganese.

The catalysts of the present invention can be unsupported or supported catalysts. Suitable support materials are, for example, oxides such as aluminum oxide, lanthanum oxide, titanium dioxide, zirconium dioxide, magnesium oxide or zinc oxide or zeolites or activated carbon or mixtures thereof.

The compositions of the present invention are advantageously obtainable by heating a precursor which comprises iron, oxygen and, if desired, one or more of the components b), c) and d) and has an atomic ratio of divalent iron to trivalent iron of not more than 0.5 in the presence of a reducing agent to at least the melting point of the precursor, cooling the resulting material to 25° C. to give a composition having a ratio of divalent iron to trivalent iron in the range from >0.5 to 5.5, preferably in the range from 0.57 to 2.2, and then reducing the composition by means of a hydrogen-containing gas at from 200 to 500° C.

The proportions of divalent iron and trivalent iron present in the precursor of the composition of the present invention is, for the purposes of the present invention, determined by measuring the proportions of crystalline phases present by X-ray diffraction on a D5000 theta/theta diffractometer (from Siemens, Germany) using TOPAS software for evaluation.

In a preferred embodiment, the precursor of the composition of the present invention comprises divalent and trivalent iron in the form of magnetite, which in the ideal case can be described by the formula $Fe_3O_4$, i.e. as $Fe(II)Fe(III)_2O_4$, and the additional divalent iron partly or wholly in the form of wüstite. In a particularly preferred embodiment, from >0 to 90%, in particular from 1.2 to 77%, of the divalent iron is present in the form of wüstite. For the purposes of the present invention, wüstite is an iron oxide of the formula $Fe_{1-x}O$ where $0 = x = 0.16$.

The wüstite content is determined for the purposes of the present invention by measuring the proportions of crystalline phases present by X-ray diffraction on a D5000 theta/theta diffractometer (from Siemens, Germany) using TOPAS software for evaluation.

The precursor of the composition of the present invention can advantageously be obtained by heating a precursor which comprises iron, oxygen and, if desired, one or more of the components b), c) and d) and has an atomic ratio of divalent iron to trivalent iron lower than that defined in a) in the presence of a reducing agent to at least the melting point of the precursor.

As iron- and oxygen-containing precursors, it is possible to use precursors comprising iron oxide, iron hydroxide or iron oxide hydroxide, for example iron(III) oxide, iron(II,III) oxide, iron(II) oxide, iron(II) hydroxide, iron(III) hydroxide or an iron oxide hydroxide such as FeOOH. It is possible to use synthetically produced or natural iron oxides, iron hydroxides or iron oxide hydroxides, e.g. magnetite, which in the ideal case can be described as $Fe_3O_4$, limonite, which in the ideal case can be described as $Fe_2O_3 \cdot H_2O$, or haematite, which in the ideal case can be described as $Fe_2O_3$.

The one or more components b), c) and d) which may optionally be present can be present in the precursor in the form of oxides, hydroxides, other salts of inorganic acids, e.g. nitrates, chlorides, carbonates or sulfates, or salts of organic acids, e.g. formates or acetates.

In a preferred embodiment, natural magnetite is employed as precursor. The composition of such a natural magnetite can, if desired, be modified by addition of one or more of the components c), d) and e).

In a further preferred embodiment, the reducing agent used is selected from the group consisting of iron, the elements specified in b), the elements specified in c), manganese, carbon and mixtures thereof, preferably selected from the group consisting of iron, aluminum, magnesium, carbon and mixtures thereof, in particular iron.

The amount of reducing agent required to set the ratio of divalent iron to trivalent iron specified according to the present invention in the oxidic composition can readily be determined by means of a few simple preliminary tests.

When iron is used as reducing agent, the addition of from 1 to 50% by weight of iron, based on the total amount of iron and oxygen present in the precursor, has been found to be particularly advantageous.

The precursor of the composition of the present invention can be converted into supported or unsupported catalysts, preferably unsupported catalysts, as are preferably used for hydrogenation, in particular for the hydrogenation of nitrile groups to amine groups, for example to convert adiponitrile partly or wholly into 6-aminocapronitrile or a mixture of 6-aminocapronitrile and hexamethylenediamine or partly or wholly into hexamethylenediamine, by treatment in a reducing atmosphere ("activation"), for example by exposing them to a hydrogen atmosphere or a gas mixture comprising hydrogen and an inert gas such as nitrogen at from 200 to 500° C., preferably from 250 to 450° C., for from 2 to 120 hours. Here, the space velocity over the catalyst is preferably from 2000 to 10 000 standard 1 per 1 of catalyst per hour.

The activation can advantageously be carried out directly in the synthesis reactor, since this usually saves an intermediate step which is otherwise necessary, namely passivation of the surface at usually from 20 to 80° C., preferably from 25 to 65° C., by means of oxygen/nitrogen mixtures, e.g. air. The activation of passivated catalysts is preferably carried out in the synthesis reactor at from 180 to 500° C., preferably from 200 to 350° C., in a hydrogen-containing atmosphere.

The catalysts can be used as fixed-bed catalysts in the upflow or downflow mode or as suspended catalysts.

As starting materials for the hydrogenation, use can advantageously be made of aliphatic alpha,omega-dinitriles of the formula

where n is an integer from 1 to 10, in particular 2, 3, 4, 5 or 6. Particularly preferred compounds are succinonitrile, glutaronitrile, adiponitrile, pimelonitrile and suberonitrile, very particular preferably adiponitrile. The above-described dinitriles are preferably partially hydrogenated in the presence of a liquid diluent and one of the abovementioned catalysts to form alpha,omega-aminonitriles of the formula

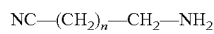

where n is as defined above.

Particularly preferred aminonitriles are ones in which n is 2, 3, 4, 5 or 6, in particular 4, i.e. 4-aminobutanonitrile, 5-aminopentanonitrile, 6-aminohexanonitrile ("6-aminocapronitrile"), 7-aminoheptanonitrile and 8-aminooctanonitrile, very particularly preferably 6-aminocapronitrile.

If the reaction is carried out in suspension, it is usual to select a temperature in the range from 40 to 150° C., preferably from 50 to 100° C., particularly preferably from 60 to 90° C.; the pressure is generally chosen so as to be in the range from 2 to 30 MPa, preferably from 3 to 30 MPa, particularly preferably from 4 to 9 MPa. The residence times depend mainly on the desired yield, selectivity and the desired conversion; the residence time is usually selected so that a maximum yield is achieved, for example in the range from 50 to 275 minutes, preferably from 70 to 200 minutes.

In a suspension hydrogenation, the liquid diluent used is preferably ammonia, an amine, a diamine or a triamine having from 1 to 6 carbon atoms in one amine side chain, e.g. trimethylamine, triethylamine, tripropylamine or tributylamine, or an alcohol, in particular methanol or ethanol, particularly preferably ammonia.

The dinitrile concentration is advantageously in the range from 10 to 90% by weight, preferably from 30 to 80% by weight, particularly preferably from 40 to 70% by weight, based on the sum of dinitrile and liquid diluent.

The amount of catalyst employed is generally in the range from 1 to 50% by weight, preferably from 5 to 20% by weight, based on the amount of dinitrile used.

The suspension hydrogenation can be carried out batchwise or preferably continuously, generally in the liquid phase.

The partial hydrogenation can also be carried out batchwise or continuously in a fixed-bed reactor in the downflow or upflow mode, generally at from 20 to 150° C., preferably from 30 to 90° C., and a pressure which is generally in the range from 2 to 40 MPa, preferably from 3 to 30 MPa. The partial hydrogenation is preferably carried out in the presence of a liquid diluent, preferably ammonia, an amine, a diamine or a triamine having from 1 to 6 carbon atoms in one amine side chain, e.g. trimethylamine, triethylamine, tripropylamine or tributylamine, or an alcohol, in particular methanol or ethanol, particularly preferably ammonia. In a preferred embodiment, the amount of ammonia is chosen so as to be in the range from 1 to 10 g, preferably from 2 to 6 g, per g of dinitrile. Preference is given to a space velocity over the catalyst in the range from 0.1 to 2.0 kg, preferably from 0.3 to 1.0 kg, of dinitrile per liter of catalyst per hour. Here too, the conversion and thus the selectivity can be adjusted by altering the residence time.

The partial hydrogenation gives a mixture comprising dinitrile, alpha,omega-aminonitrile and alpha,omega-diamine. Complete hydrogenation gives a mixture comprising alpha, omega-diamine.

The desired product or products can be separated from these mixtures in a manner known per se for such mixtures, for example by distillation or extraction. Such separation processes are described, for example, in WO 96/20166, WO 98/11059, WO 99/44983 and WO 99/44984.

EXAMPLES

Example 1

Preparation of an Oxidic Composition According to the Present Invention

The composition was prepared by melting a mixture of 900 kg of natural magnetite and 75 kg of iron powder at 1550° C. in air. After the melt had been cooled to room temperature and solidified, the composition was made up of the following:

72% by weight of iron, 0.17% by weight of manganese, 0.08% by eight of aluminum, 0.03% by weight of calcium, 0.05% by weight of magnesium, 0.12% by weight of silicon, 0.01% by weight of titanium, balance oxygen. The wüstite content was 44%, based on the total weight. The atomic ratio of divalent iron to trivalent iron was 1.76.

Example 2

Preparation of a Catalyst

The composition as described in example 1 was comminuted in a jaw crusher. A sieve fraction of 1.5-3 mm was screened out and reduced in a stream of hydrogen/nitrogen at 450° C. for 72 hours. After cooling under nitrogen, the catalyst was passivated using a mixture of 1% of air in nitrogen for a period of 24 hours, with the temperature in the catalyst bed being kept below 65° C. during this exothermic reaction.

The average mean crystallite size of the iron was 29.5 nm.

Example 3

Hydrogenation of Adiponitrile in a Fixed Bed

Three tube reactors connected in series (total length=4.5 m, d=6 mm) were charged with 141 ml (239 g) of the catalyst prepared as described in example 2 (1.5-3 mm size fraction) and subsequently reduced in a stream of hydrogen at atmospheric pressure (200 l/h). For this purpose, the temperature was increased from 70° C. to 340° C. over a period of 24 hours and subsequently held at 340° C. for 72 hours. After reducing the temperature, a mixture of 75.0 ml/h of ADN (adiponitrile), 370 ml/h of $NH_3$ and 200 standard l/h of $H_2$ was fed into the reactor at 250 bar.

Under the stated conditions, the following results were obtained as a function of the temperature:

| Temp. [° C.] | ADN conversion [%] | ACN selectivity [%] | HMD selectivity [%] | ACN + HMD selectivity [%] |
|---|---|---|---|---|
| 80 | 57.9 | 79.58 | 19.37 | 99.0 |
| 90 | 73.0 | 71.0 | 28.0 | 99.0 |
| 107 | 100.0 | 0.9 | 98.9 | 99.8 |

Comparative Example 1

Preparation of the Catalyst

A catalyst was prepared as described in WO 98/11059, example 2a.

The average mean crystallite size of the iron was 37 nm.

Comparative example 2

Hydrogenation of Adiponitrile in a Fixed Bed

Using the catalyst prepared in comparative example 1, adiponitrile was hydrogenated in a fixed bed as described in WO 98/11059, example 2b.

The following results were obtained:

| Temp. [° C.] | ADN conversion [%] | ACN selectivity [%] | HMD selectivity [%] | ACN + HMD selectivity [%] |
|---|---|---|---|---|
| 80 | 47.3 | 80.48 | 18.57 | 98.9 |
| 90 | 72.1 | 67.3 | 31.7 | 99.0 |
| 107 | 99.9 | 0.6 | 98.6 | 99.2 |

We claim:

1. A process for hydrogenating a nitrile group in a compound containing a nitrile group to form an amino group in the presence of a catalyst, wherein the catalyst used is a composition which comprises
    a) iron or a mixture comprising iron and a compound based on iron, wherein the iron has an average mean crystallite size in the range from 1 to 35 nm, measured by means of X-ray diffraction.

2. A process as claimed in claim 1, wherein the composition further comprise
    b) from 0.01 to 5% by weight, based on a), of a promoter based on 1, 2, 3, 4 or 5 elements selected from the group consisting of aluminum, silicon, zirconium, titanium and vanadium and
    c) from 0 to 0.5% by weight, based on a), of a compound based on an alkali metal or alkaline earth metal.

3. A process as claimed in claim 1, wherein the composition further comprises
    b) from 0.01 to 5% by weight, based on a), of a promoter based on 1, 2 or 3 elements selected from the group consisting of aluminum, silicon and vanadium and
    c) from 0 to 0.5% by weight, based on a), of a compound based on an alkali metal or alkaline earth metal.

4. A process as claimed in claim 1, wherein the composition further comprises c) from 0 to 0.5% by weight, based on a), of a compound based on an alkali metal or alkaline earth metal.

5. A process as claimed in claim 1, wherein the composition further comprises d) from 0.001 to 0.1% by weight of manganese in the form of a compound based on manganese.

6. A process as claimed in claim 1, wherein the composition is in form of an unsupported catalyst.

7. A process as claimed in claim 1, wherein the composition is combined with a support to form a supported catalyst.

8. A process as claimed in claim 1, wherein the compound containing a nitrile group which is used is adiponitrile.

9. A process as claimed in claim 1, wherein adiponitrile is partly or wholly hydrogenated to 6-aminocapronitrile.

10. A process as claimed in claim 1, wherein adiponitrile is partly or wholly hydrogenated to hexamethylenediamine.

11. A process as claimed in claim 1, wherein the iron has an average mean crystallite size in the range from 1 to 30 nm, measured by means of X-ray diffraction.

12. A process as claimed in claim 2, wherein the compound based on an alkali metal or alkaline earth metal selected from the group consisting of lithium, sodium, potassium, rubidium, cesium, magnesium, calcium, and mixtures thereof.

13. A process as claimed in claim 7, wherein the support is selected from the group consisting of oxides, zeolites, activated carbon, and combinations thereof.

14. A process as claimed in claim 7, wherein the support is selected from the group consisting of aluminum oxide, lanthanum oxide, titanium dioxide, zirconium dioxide, magnesium oxide, zinco oxide, and combinations thereof.

15. A process as claimed in claim 1, wherein the compound containing a nitrile group is an aliphatic alpha, omega-dinitrile of the formula

$$NC-(CH_2)_n-CN$$

wherein n is an integer from 1 to 10.

16. A process as claimed in claim 1, wherein the hydrogenation reaction is carried out in suspension at a temperature in the range from 40 to 150° C., at a pressure in the range of from 2 to 30 MPa, and wherein the residence time is from 50 to 275 minutes.

17. A process as claimed in claim 16, wherein a liquid diluent is employed, and wherein the liquid diluent is selected from the group consisting of ammonia, an amine, a diamine, a triamine having from 1 to 6 carbon atoms in one amine side chain, and an alcohol.

18. A process as claimed in claim 1, wherein the compound containing a nitrile group is an aliphatic alpha, omega-dinitrile of the formula

$$NC-(CH_2)_n-CN$$

wherein n is an integer from 1 to 10, wherein the hydrogenation reaction is carried out in suspension, wherein a liquid diluent is employed, and wherein the dinitrile concentration is in the range from 10 to 90% by weight based on the sum of dinitrile and liquid diluent.

19. A process as claimed in claim 18, wherein the amount of catalyst employed is in the range of from 1 to 50% by weight based on the amount of dinitrile.

20. A process as claimed in claim 1, wherein the hydrogenation is a partial hydrogenation, giving a mixture comprising dinitrile, alpha,omega-aminonitrile, and alpha,omega-diamine.

* * * * *